(12) United States Patent
Wilsey

(10) Patent No.: US 9,592,243 B2
(45) Date of Patent: *Mar. 14, 2017

(54) MEDICAL DEVICES AND METHODS COMPRISING AN ANABOLIC AGENT FOR TREATMENT OF AN INJURY

(71) Applicant: Warsaw Orthopedic, Inc., Warsaw, IN (US)

(72) Inventor: Jared T. Wilsey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/085,444

(22) Filed: Nov. 20, 2013

(65) Prior Publication Data

US 2014/0107088 A1 Apr. 17, 2014

Related U.S. Application Data

(63) Continuation-in-part of application No. 13/093,479, filed on Apr. 25, 2011.

(51) Int. Cl.
*A61K 31/58* (2006.01)
*A61K 47/34* (2006.01)
(Continued)

(52) U.S. Cl.
CPC ............. *A61K 31/58* (2013.01); *A61K 38/27* (2013.01); *A61K 38/28* (2013.01); *A61K 38/30* (2013.01);
(Continued)

(58) Field of Classification Search
CPC .... A61L 2400/06; A61L 31/06; A61L 31/148; A61L 31/16; A61L 26/0019;
(Continued)

(56) References Cited

U.S. PATENT DOCUMENTS 4,624,255 A 11/1986 Schenck et al.
4,742,054 A 5/1988 Naftchi
(Continued)

FOREIGN PATENT DOCUMENTS

WO 03005961 A2 1/2003
WO 2005034998 A2 4/2005
WO 2007005177 A1 1/2007

OTHER PUBLICATIONS

Chhipa et al "Formulation Optimization of Sustained Release Pellets of Itopride Hydrochloride using Different Polymers," Journal of Pharmacy Research 2009 2(8) 1404-1408).*
(Continued)

*Primary Examiner* — Suzanne Ziska

(57) ABSTRACT

Improved medical devices and methods are provided comprising an anabolic agent for healing an injury. These improved medical devices and methods can enhance healing in injuries from traumatic soft tissue injury, surgical injuries, burn, traumatic brain injuries, musculotendinous injuries, musculoskeletal conditions, bone injury or other injuries or maladies, which can be chronic or non-chronic in origin. In some embodiments, the medical device comprises a drug depot that releases the anabolic agent over at least 2 days to enhance healing of an injury.

8 Claims, 1 Drawing Sheet

(51) Int. Cl.
| | |
|---|---|
| A61L 26/00 | (2006.01) |
| A61K 38/27 | (2006.01) |
| A61K 38/28 | (2006.01) |
| A61K 38/30 | (2006.01) |
| A61L 31/06 | (2006.01) |
| A61L 31/14 | (2006.01) |
| A61L 31/16 | (2006.01) |

(52) U.S. Cl.
CPC ............ *A61K 47/34* (2013.01); *A61L 26/009* (2013.01); *A61L 26/0019* (2013.01); *A61L 26/0066* (2013.01); *A61L 31/06* (2013.01); *A61L 31/148* (2013.01); *A61L 31/16* (2013.01); *A61L 2300/222* (2013.01); *A61L 2300/414* (2013.01); *A61L 2300/43* (2013.01); *A61L 2300/604* (2013.01); *A61L 2400/06* (2013.01)

(58) Field of Classification Search
CPC ............... A61L 26/009; A61L 26/0066; A61L 2300/222; A61L 2300/414; A61L 2300/43; A61L 2300/604; A61K 38/27; A61K 38/28; A61K 38/30; A61K 47/34; A61K 31/58; C08L 67/04
See application file for complete search history.

(56) References Cited

U.S. PATENT DOCUMENTS

| | | | |
|---|---|---|---|
| 4,863,457 | A | 9/1989 | Lee |
| 5,522,844 | A | 6/1996 | Johnson |
| 5,571,882 | A | 11/1996 | Vetter |
| 5,626,838 | A | 5/1997 | Cavanaugh, Jr. |
| 5,707,647 | A | 1/1998 | Dunn et al. |
| 5,759,583 | A | 6/1998 | Iwamoto et al. |
| 5,868,789 | A | 2/1999 | Huebner |
| 5,942,241 | A | 8/1999 | Chasin et al. |
| 6,069,129 | A | 5/2000 | Sandberg et al. |
| 6,179,862 | B1 | 1/2001 | Sawhney |
| 6,248,345 | B1 | 6/2001 | Goldenheim et al. |
| 6,287,588 | B1 | 9/2001 | Shih et al. |
| 6,326,020 | B1 | 12/2001 | Kohane et al. |
| 6,331,311 | B1 | 12/2001 | Brodbeck et al. |
| 6,428,804 | B1 | 8/2002 | Suzuki et al. |
| 6,461,631 | B1 | 10/2002 | Dunn et al. |
| 6,524,607 | B1 | 2/2003 | Goldenheim et al. |
| 6,534,081 | B2 | 3/2003 | Goldenheim et al. |
| 6,589,549 | B2 | 7/2003 | Shih et al. |
| 6,616,946 | B1 | 9/2003 | Meier et al. |
| 6,630,155 | B1 | 10/2003 | Chandrashekar et al. |
| 6,632,457 | B1 | 10/2003 | Sawhney |
| 6,652,883 | B2 | 11/2003 | Goupil et al. |
| 6,676,971 | B2 | 1/2004 | Goupil et al. |
| 6,710,126 | B1 | 3/2004 | Hirt et al. |
| 6,723,741 | B2 | 4/2004 | Jeon et al. |
| 6,723,814 | B2 | 4/2004 | Meier et al. |
| 6,756,058 | B2 | 6/2004 | Brubaker et al. |
| 6,773,714 | B2 | 8/2004 | Dunn et al. |
| 6,921,541 | B2 | 7/2005 | Chasin et al. |
| 6,974,462 | B2 | 12/2005 | Sater |
| 7,070,809 | B2 | 7/2006 | Goupil et al. |
| 7,144,412 | B2 | 12/2006 | Wolfe et al. |
| 7,166,570 | B2 | 1/2007 | Hunter et al. |
| 7,220,281 | B2 | 5/2007 | Lambrecht et al. |
| 7,229,441 | B2 | 6/2007 | Trieu et al. |
| 7,235,043 | B2 | 6/2007 | Gellman et al. |
| 7,287,983 | B2 | 10/2007 | Ilan |
| 7,318,840 | B2 | 1/2008 | McKay |
| 7,329,259 | B2 | 2/2008 | Cragg |
| 7,361,168 | B2 | 4/2008 | Makower et al. |
| 7,367,978 | B2 | 5/2008 | Drewry et al. |
| 7,829,110 | B2 | 11/2010 | Wohlert |
| 8,470,360 | B2 * | 6/2013 | McKay .................. 424/426 |
| 2002/0009454 | A1 | 1/2002 | Boone et al. |
| 2002/0090398 | A1 | 7/2002 | Dunn et al. |
| 2002/0122771 | A1 | 9/2002 | Holland et al. |
| 2002/0127269 | A1 | 9/2002 | Waring et al. |
| 2003/0022927 | A1 | 1/2003 | Jeon et al. |
| 2003/0185873 | A1 | 10/2003 | Chasin et al. |
| 2003/0203044 | A1 | 10/2003 | Moravec |
| 2003/0204191 | A1 | 10/2003 | Sater et al. |
| 2003/0224033 | A1 | 12/2003 | Li et al. |
| 2004/0072799 | A1 | 4/2004 | Li et al. |
| 2004/0082540 | A1 | 4/2004 | Hermida Ochoa |
| 2004/0097468 | A1 | 5/2004 | Sunil |
| 2004/0109893 | A1 | 6/2004 | Chen et al. |
| 2004/0214793 | A1 | 10/2004 | Hermida Ochoa |
| 2005/0059744 | A1 | 3/2005 | Donello et al. |
| 2005/0129656 | A1 | 6/2005 | Goupil et al. |
| 2005/0142163 | A1 | 6/2005 | Hunter et al. |
| 2005/0175709 | A1 | 8/2005 | Baty, III et al. |
| 2005/0186261 | A1 | 8/2005 | Avelar et al. |
| 2005/0197293 | A1 | 9/2005 | Mellis et al. |
| 2005/0222684 | A1 | 10/2005 | Ferree |
| 2005/0287218 | A1 | 12/2005 | Chaouk et al. |
| 2005/0288789 | A1 | 12/2005 | Chaouk et al. |
| 2006/0074422 | A1 | 4/2006 | Story et al. |
| 2006/0106361 | A1 | 5/2006 | Muni et al. |
| 2006/0147488 | A1 * | 7/2006 | Wohlert .................. 424/423 |
| 2006/0148903 | A1 | 7/2006 | Burch et al. |
| 2006/0183786 | A1 | 8/2006 | Wang |
| 2006/0189944 | A1 | 8/2006 | Campbell et al. |
| 2006/0228391 | A1 | 10/2006 | Seyedin et al. |
| 2007/0004790 | A1 | 1/2007 | Chow et al. |
| 2007/0066568 | A1 * | 3/2007 | Dalton et al. .................. 514/80 |
| 2007/0093907 | A1 | 4/2007 | Goupil et al. |
| 2007/0150061 | A1 | 6/2007 | Trieu |
| 2007/0156180 | A1 | 7/2007 | Jaax et al. |
| 2007/0185497 | A1 | 8/2007 | Cauthen et al. |
| 2007/0202074 | A1 | 8/2007 | Shalaby |
| 2007/0243225 | A1 | 10/2007 | McKay |
| 2007/0243228 | A1 | 10/2007 | McKay |
| 2007/0248639 | A1 | 10/2007 | Demopulos et al. |
| 2007/0253994 | A1 | 11/2007 | Hildebrand |
| 2008/0021074 | A1 | 1/2008 | Cartt |
| 2008/0085263 | A1 | 4/2008 | Krister et al. |
| 2008/0091207 | A1 | 4/2008 | Truckai et al. |
| 2008/0097229 | A1 | 4/2008 | Roy et al. |
| 2008/0269717 | A1 | 10/2008 | Crandall et al. |
| 2009/0020076 | A1 | 1/2009 | Ghiraldi |
| 2009/0048678 | A1 | 2/2009 | Saal et al. |
| 2009/0143333 | A1 | 6/2009 | Palefsky et al. |
| 2009/0202645 | A1 | 8/2009 | Predieri |
| 2009/0222096 | A1 | 9/2009 | Trieu |
| 2009/0246123 | A1 | 10/2009 | Zanella et al. |
| 2009/0263319 | A1 | 10/2009 | Wohabrebbi et al. |
| 2009/0263489 | A1 | 10/2009 | Zanella |
| 2009/0264489 | A1 | 10/2009 | Hildebrand et al. |
| 2009/0275913 | A1 | 11/2009 | Trieu |
| 2010/0239632 | A1 | 9/2010 | Walsh |

OTHER PUBLICATIONS

American Burn Association, Burn Incidence and Treatment in the United States: 2011 Fact Sheet, 1 pg.
QLT, Inc., Atrigel, Drug Delivery Platform, www.qltinc.com, Fort Collins, CO, U.S., Jul. 2006, 2 pgs.
Lynda Cole, RN and Caroline Nesbitt, RN, A Three-Year Multiphase Pressure Ulcer Prevalence/Incidence Study in a Regional Referral Hospital, vol. 57, Issue 1, Jan. 2011, pp. 1-5.
Robert H. Demling, MD., Oxandrolone, an anabolic steroid, enhances the healing of a cutaneous wound in the rat, Wound Repair and Regeneration, Mar.-Apr. 2000, Boston, MA pp. 97-102.
Robert H. Demling, MD., The Role of Anabolic Hormones for Wound Healing in Catabolic States, Journal of Burns and Wounds, www.JOURNALOFBURNSANDWOUNDS.COM, Burn Center, Brigham & Women's Hospital, Boston, MA, and Harvard Medical School, Boston, MA, 2005, vol. 4, pp. 46-62.
William H. Eaglstein, M.D., Patricia Mertz, B.A. and Oscar M. Alvarez, Ph.D., Effect of Topically Applied Agents on Healing

(56) References Cited

OTHER PUBLICATIONS

Wounds, Dept. of Dermatology, Univ. of Pittsburgh School of Medicine, Pittsburgh, PA, and Cornell Univ. Mecial Center, New York, NY, Jul.-Sep. 1984, vol. 2, No. 3, pp. 112-115.

Helena Cristina Franciso Pereira Da Silva, Rodrigo Cecanho, Cephalometric changes produced by locally applied anabolic steroid in Wistar rats, Archives of Oral Biology 54 (2009) pp. 389-395.

Daniel P. Moore, M.D., Helping your patients with spasticity reach maximal function, vol. 104, No. 2, Aug. 1998, Postgradute Medicine, http://www.postgradmed.com/issues/1998/08_98/moore.htm, pp. 1-9.

James Witherspoon, Car Accident Injury Trends For 1999-2008, http://EzineArticles.com/?expert=James_Witherspoon, 2 pages.

Elizabeth A. Moberg-Wolff, M.D., Dept. of Physical Medicine and Rehabilitation, Medical College of Wisconsin, Consulting Staff, Dept of Physical Medicine and Rehabilitation, Children's Hospital of Wisconsin, Spasticity; Article last Updated: Dec. 21, 2007, pp. 1-15.

International Search Report and Written Opinion for PCT/US2012/027464, the counterpart application mailed on Sep. 19, 2012.

\* cited by examiner

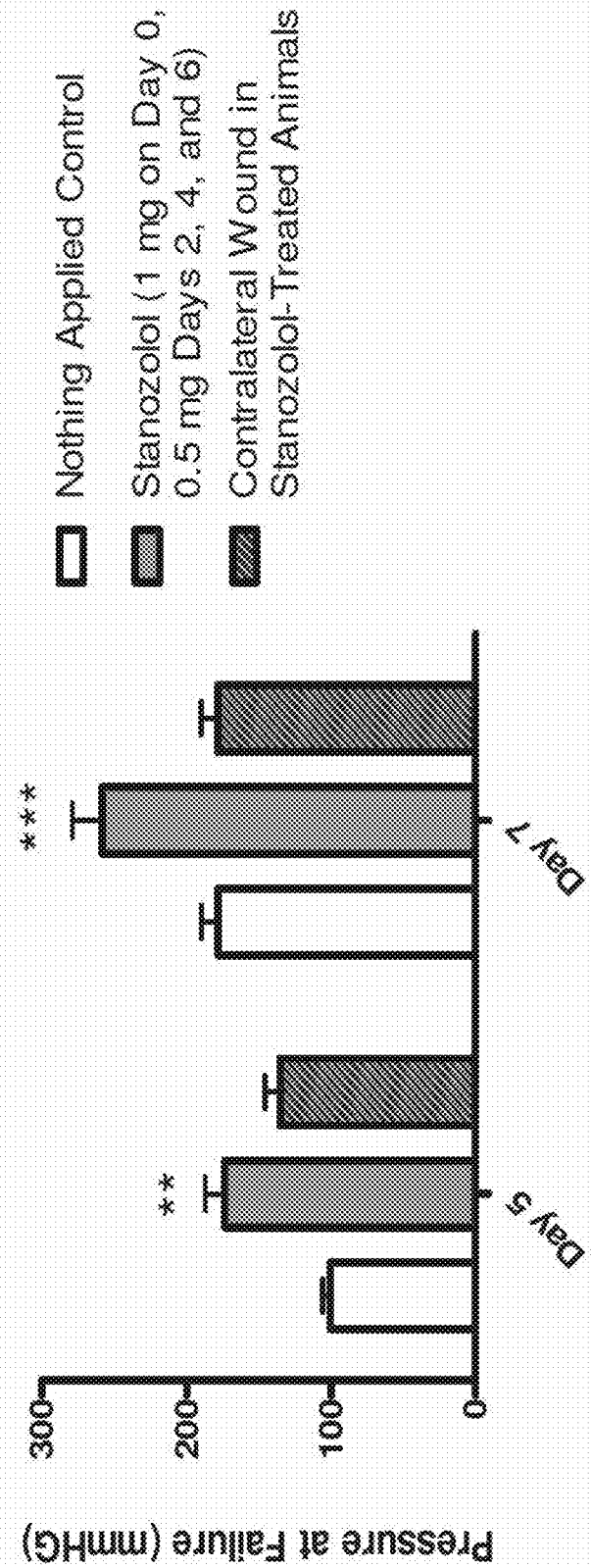

MEDICAL DEVICES AND METHODS COMPRISING AN ANABOLIC AGENT FOR TREATMENT OF AN INJURY

CROSS REFERENCE TO RELATED APPLICATIONS

This application claims priority to and is a continuation in part of U.S. application Ser. No. 13/093,479, filed on Apr. 25, 2011, the entire contents of which is incorporated herein by reference in its entirety.

BACKGROUND

Injury can occur from various types of conditions such as musculoskeletal conditions, musculotendinous injuries, bone injury, surgical injuries, traumatic brain injuries, traumatic soft tissue injuries, and burns. Several musculoskeletal conditions are made chronic by failure of the involved muscles and tendons to heal from injury. The healing rate of an injury can be improved by controlling the environment around the injury during the healing process. Many injury treatments involve cleaning the injury and debriding it, and often, covering it with a dressing to help it heal faster.

Commonly used dressings include gauzes, foams, sponges, cotton wads or other fibrous materials. Gauzes and other fibrous materials are used to absorb fluids by capillary action to remove exudates from the injury and prevent influx of bacteria and other pathogens while the injury heals. Often, dressings are normally draped over the treatment site and held in place by sutures or adhesives. However, the suturing of these dressings in place is often tedious and time-consuming and not desirable in many body sites. Adhesives used in injury healing are normally used external to the body and not applied directly to the damaged tissue but to adjacent healthy tissue because they must be removed. Sometimes tissue can grow into the dressing as the injury heals, but this tissue is torn when the dressing is removed causing greater injury, which causes further delays in healing.

Other materials have been used alone or in conjunction with dressings, such as gels hydrogels, granules and pastes to promote healing by keeping the injury bed moist, cleaning the injury, and also removing necrotic matter from it by fluid donation. These materials may also absorb exudate from the injury. However, there is a need to develop improved injury healing therapies that enhance the healing of injuries.

Anabolic agents are a class of pharmaceutical compounds known to the medical profession for their properties of increasing muscles mass and body weight. These properties of building up muscle mass and weight are beneficial for patients with decreased muscle mass and weight loss experienced in patients with conditions such as cancer, HIV or other muscle wasting syndromes. Anabolic steroids also have been used by the medical profession to stimulate puberty and growth in children and for hormone replacement therapy.

Anabolic steroids can be represented by the following general structure:

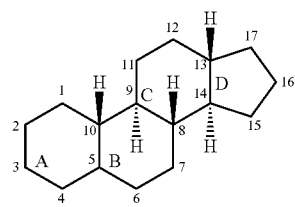

Testosterone is an example of a naturally occurring anabolic steroid that exhibits the above general structure except it has a double bonded oxygen at position 3 of the A ring and a hydroxyl group at position 17 on the D ring. Many modifications of the above general structure to various positions in the A, B, C and/or D rings have been made to increase binding activity to the steroid receptor and to increase lipid solubility of the anabolic steroids and prolong its activity. For example, alkylation at 17-alpha position with methyl or ethyl groups create orally active compounds because it slows the degradation of the drug by the liver. Esterification at the 3 and/or 17 positions allow the anabolic steroid compound to be activated in the blood stream when parenterally administered and also increases the duration of effectiveness by increasing the lipid solubility. Alterations of the ring structure also allow different anabolic steroid compounds to have different anabolic to androgenic effects.

Although anabolic agents are conventionally used to increase muscles mass and body weight, to date, they have not been widely appreciated for local administration for healing injuries. Therefore, there is a need for improved medical devices and methods comprising an anabolic agent for healing injuries.

SUMMARY

Improved medical devices and methods are provided comprising an anabolic agent for healing injuries. These improved medical devices and methods can enhance healing in injuries from musculoskeletal conditions, musculotendinous injuries, bone injury, surgical injuries, traumatic brain injuries, traumatic soft tissue injuries and burns, or other injuries or maladies, which can be chronic or non-chronic in origin.

In one embodiment, there is an implantable medical device for treating an injury in a patient in need of such treatment, the implantable medical device comprising an anabolic agent, and at least one biodegradable polymer. In some embodiments, the medical device has a surface that releases about 50% to about 90% of the anabolic agent relative to a total amount of the anabolic agent loaded in the medical device over a first period of up to 24 hours. In some embodiments, the medical device has a surface that releases about 10% to about 50% of the anabolic agent relative to a total amount of the anabolic agent loaded in the medical device over a subsequent period of at least 2 days.

In another embodiment, there is an implantable drug depot for treating an injury in a patient in need of such treatment, the implantable drug depot comprising an anabolic agent, and at least one biodegradable polymer. In some embodiments, the implantable drug depot has a surface that releases about 30% to about 50% of the anabolic agent relative to a total amount of the anabolic agent loaded in the drug depot over a first period of up to 12 hours. In some embodiments, the implantable drug depot has a surface that releases about 50% to about 70% of the anabolic agent relative to a total amount of the anabolic agent loaded in the drug depot over a subsequent period of at least 2 days.

In yet another embodiment, there is a method for treating an injury in a patient in need of such treatment, the method comprising administering an anabolic agent locally at or near the injury, the anabolic agent being administered by a topical formulation, an infusion pump or local injection over a period of at least one day so as to enhance healing of the injury.

The medical device may: (i) consist of only the anabolic agent (or one or more of its pharmaceutically acceptable salts, esterified forms or non-esterified forms thereof) and the biodegradable polymer(s); or (ii) consist essentially of the anabolic agent (and/or one or more of its pharmaceutically acceptable salts, esterified forms or non-esterified forms thereof) and the biodegradable polymer(s); or (iii) comprise the anabolic agent (and/or one or more of its pharmaceutically acceptable salts, esterified forms or non-esterified forms thereof), and the biodegradable polymer(s) and one or more other active ingredients, surfactants, excipients or other ingredients or combinations thereof. When there are other active ingredients, surfactants, pore forming agents, plasticizers, excipients or other ingredients or combinations thereof in the formulation, in some embodiments these other compounds or combinations thereof comprise less than 50 wt. %. less than 40 wt. %, less than 30 wt. %, less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWING

In part, other aspects, features, benefits and advantages of the embodiments will be apparent with regard to the following description, appended claims and accompanying drawing where:

FIG. 1 is a bar graph illustration of accelerated surgical injury healing demonstrated in animals that received a locally injected anabolic agent (stanozolol) at a bolus dose of 1 mg initially, then 0.5 mg on days 2, 4, and 6. The surgical injuries were tested on days 5 and seven. The surgical injuries that received locally delivered stanozolol had the highest injury strength when exposed to pressure when compared to injuries with the control or placebo administered to them.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

The term "implantable" as utilized herein refers to a biocompatible medical device (e.g., drug depot) retaining potential for successful placement within a mammal. The expression "implantable medical device" and expressions of the like import as utilized herein refers to an object implantable through surgery, injection, or other suitable means whose primary function is achieved either through its physical presence or mechanical properties.

A "drug depot" is the composition in which the anabolic agent is administered to the injury. Thus, a drug depot may comprise a physical structure to facilitate implantation and retention in a desired site (e.g., muscle, tendon, bone, surgical injury, traumatic brain injuries, traumatic soft tissue injuries, burns, etc.). The drug depot may also comprise the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.01 cm to about 20 cm from the administration site and comprises the anabolic agent. In some embodiments, the optimal drug concentration gradient of the therapeutic agent at a distance of up to about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 or 20 cm from the administration site and comprises the anabolic agent. In various embodiments, a drug depot may also include a pump or pellet.

A "therapeutically effective amount" or "effective amount" is such that when administered, the drug results in alteration of the biological activity, such as, for example, inhibition of inflammation, improvement in the healing of the injury, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments, all or parts (e.g., surfaces, regions, layers, etc.) of the medical device (e.g., drug depot) may be designed for immediate release. In other embodiments the medical device (e.g., drug depot) may be designed for sustained release. In other embodiments, the medical device (e.g., drug depot) comprises one or more immediate release surfaces, layers, regions and one or more sustained release surfaces layers or regions.

The term "biodegradable" includes that all or parts of the medical device (e.g., drug depot) will degrade over time by the action of enzymes, by hydrolytic action and/or by other similar mechanisms in the human body. In various embodiments, "biodegradable" includes that the depot (e.g., microparticle, microsphere, etc.) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

In some embodiments, the medical device (e.g., drug depot) has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. In some embodiments, the pores in the drug depot will be less than 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495 and/or 500 microns. This pore size will prevent cells from infiltrating the drug depot and laying down scaffolding cells. Thus, in this embodiment, drug will elute from the drug depot as fluid enters the drug depot, but cells will be prevented from entering. Pores can be made using, for example a pore forming agent including polyhydroxy compounds such as a carbohydrate, a polyhydroxy aldehyde, a polyhydroxy ketone, a glycogen, an aldose, a sugar, a mono- or polysaccharide, an oligosaccharide, a polyhydroxy carboxylic compound, polyhydroxy ester compound, a cyclodextrin, a polyethylene glycol polymer, a glycerol an alginate, a chitosan, a polypropylene glycol polymer, a polyoxyethylene-polyoxypropylene block co-polymer, agar, or hyaluronic acid or polyhydroxy derivative compounds, hydroxypropyl cellulose, tween, sorbitan, sorbitan monolaurate, sorbitan monopalmitate, sorbitan monostearate, sorbitan tristearate, sorbitan monooleate, or a combination thereof. In some embodiments, where there are little or no pores, the drug will elute out from the drug depot by the action of enzymes, by hydrolytic action and/or by other similar mechanisms in the human body.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the medical device (e.g., drug depot), or a matrix or component thereof, or as the result of metabolic transformation or dissolution of the therapeutic agent(s) or conjugates of therapeutic agent(s). In some embodiments the medical device (e.g., drug depot) can have one or more sustained release surface(s), region(s) or layer (s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. In some embodiments the medical device (e.g., drug depot) can have one or more immediate release surface (s), regions(s) or layer(s).

The two types of formulations (sustain release and immediate release) may be used in conjunction. The sustained release and immediate release may be in one or more of the same medical device (e.g., depot). In various embodiments, the sustained release and immediate release may be part of separate depots. For example a bolus or immediate release formulation of anabolic agent may be placed at or near the target site and a sustain release formulation may also be placed at or near the same site. Thus, even after the bolus becomes completely accessible, the sustain release formulation would continue to provide the active ingredient for the intended tissue.

In various embodiments, the drug depot can be designed to cause an initial burst dose of therapeutic agent within the first twenty-four, forty-eight hours, or seventy-two hours after implantation. "Initial burst" or "burst effect" or "bolus dose" refers to the release of therapeutic agent from the medical device (e.g., one or more surfaces, regions or layers of the drug depot) during the first twenty-four hours, or forty-eight or seventy-two hours after the device comes in contact with an aqueous fluid (e.g., synovial fluid, cerebral spinal fluid, injury fluid, saline, blood etc.). In some embodiments, the medical device (e.g., weight of the drug depot) releases 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% of the total weight of the anabolic agent loaded in the medical device within the first six, twelve, eighteen, twenty-four, forty-eight, or seventy-two hours after implantation when the device comes into contact with bodily fluid. The "burst effect" or "bolus dose" is believed to be due to the increased release of therapeutic agent from the device (e.g., drug depot). In alternative embodiments, the medical device (e.g., drug depot) is designed to avoid or reduce this initial burst effect (e.g., by applying an outer polymer coating to the depot or imbedding drug deep within the polymer, or using a polymer having a high molecular weight or combinations thereof, etc.).

As used herein, the term "injury" includes, but not be limited to, various types of musculoskeletal conditions, musculotendinous injuries, bone injury, surgical injuries, traumatic brain injuries, traumatic soft tissue injuries, and burns or other injuries or maladies, which can be chronic or non-chronic.

"Treating" or "treatment" of a disease or condition refers to executing a protocol that may include administering one or more medical devices (e.g., drug depots) or drugs to a patient (human, other normal or otherwise or other mammal), in an effort to enhance or improve injury healing.

Alleviation can occur prior to signs or symptoms of the injury healing. In addition, treating or treatment does not require complete injury healing, does not require a cure, and specifically includes protocols that have only a marginal effect on injury healing of the patient. In some embodiments, the treatment can enhance or improve injury healing by 10%, 15%, 20%, 25%, 30%, 35%, 40%, 45%, 50%, 55%, 60%, 65%, 70%, 75%, 80%, 85%, 90%, 95%, or higher. For example, after local administration of the anabolic agent, the injury can heal in half the time 50% faster as compared to an injury with no anabolic agent treatment. The injury can be monitored for enhanced healing by methods known in the art such as, for example, Sussman Injury Healing Tools (SWHT), the Pressure Ulcer Scale (PUSH), Bates-Jensen Injury Assessment Tool (BWAT), Pressure Status Tools (PSST) and other methods to evaluate tissue attributes and/or surrounding skin. In some embodiments, the injury can be evaluated using a BTC-2000 device available from Surgical Research Laboratories, Inc. (Tennessee, USA) that applies negative pressure to the injury (mmHg & mb) and the integrity of the injury measured using, among other things, a laser scanner. However, other methods can be used or the injury can be observed for increased healing. Successful healing of an injury involves the coordination of multiple physiological processes, such as inflammation, cell migration, angiogenesis, formation of granulation tissue and/or tissue remodeling. In some embodiments, by administering the anabolic agent locally at, near or in the injury, injury healing is enhanced and the injury heals faster (e.g., within 1 week, 2 weeks, 3 weeks, or 4 weeks).

In some embodiments, the anabolic agent can be used to treat one or more target tissue sites including the epidermis, dermis, lower dermis, muscle, oil and sweat glands, nerves, tendons, ligaments, organs or the like that can have injuries.

"Localized" delivery includes delivery where one or more medical devices are deposited within a tissue, for example, epidermis, dermis, lower dermis, muscle, oil and sweat glands, tendons, ligaments, organs etc. or in close proximity (within about 0.1 cm, or preferably within about 5 cm, for example) thereto. For example, the medical device containing a drug can deliver a dose of it locally that is 5%, 10%, 15%, 20%, 25%, 30%, 35%, 40%, 45%, 50%, 55%, 60%, 65%, 70%, 75%, 80%, 85%, 90%, 95%, 99%, 99.9% or 99.999% less than the oral dosage or IV or IM systemic dose. In turn, systemic side effects, such as for example, liver transaminase elevations, hepatitis, liver failure, myopathy, constipation, etc. may be reduced or eliminated.

The term "mammal" refers to organisms from the taxonomy class "mammalian," including but not limited to humans, other primates such as chimpanzees, apes, orangutans and monkeys, rats, mice, cats, dogs, cows, pigs, guinea pigs, horses, etc.

The phrase "pain management medication" includes one or more therapeutic agents that are administered in addition to the anabolic steroid to prevent, alleviate or remove pain entirely. These include anti-inflammatory agents, muscle relaxants, analgesics, anesthetics, narcotics, and so forth, or combinations thereof.

The phrase "release rate profile" refers to the percentage of active ingredient that is released over fixed units of time, e.g., mcg/hr, mcg/day, mg/day, 10% per day for ten days, etc. As persons of ordinary skill know, a release rate profile may, but need not, be linear. By way of a non-limiting example, the medical device (e.g., drug depot) may be a ribbon-like fiber that releases the anabolic agent at or near the injury over a period of time.

The term "solid" is intended to mean a rigid material, while, "semi-solid" is intended to mean a material that has some degree of flexibility, thereby allowing the depot to bend and conform to the surrounding tissue requirements. In some embodiments, the medical device has a sufficient flexibility to allow placement within the injury. In some embodiments, the medical device is provided that hardens or stiffens after delivery. Typically, hardening formulations may have a pre-dosed modulus of elasticity in the range of about $1 \times ^-10^2$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening formulations (after delivery), in some embodiments, may have a rubbery consistency and have a modulus of elasticity in the range of about $1 \times ^-10^2$ to about $2 \times 10^6$ dynes/cm$^2$, or $1 \times 10^5$ to about $7 \times 10^5$ dynes/cm$^2$, or $2 \times 10^5$ to about $5 \times 10^5$ dynes/cm$^2$.

"Targeted delivery system" provides delivery of one or more medical devices (e.g., drugs depots) having a quantity of therapeutic agent that can be deposited at or near the target site as needed for treatment of the injury.

In some embodiments, the medical device may comprise DLG. The abbreviation "DLG" refers to poly(DL-lactide-co-glycolide). In some embodiments, the medical device may comprise DL. The abbreviation "DL" refers to poly (DL-lactide). In some embodiments, the medical device may comprise LG. The abbreviation "LG" refers to poly(L-lactide-co-glycolide). In some embodiments, the medical device may comprise CL. The abbreviation "CL" refers to polycaprolactone. In some embodiments, the medical device may comprise DLCL. The abbreviation "DLCL" refers to poly(DL-lactide-co-caprolactone). In some embodiments, the medical device may comprise LCL. The abbreviation "LCL" refers to poly(L-lactide-co-caprolactone). In some embodiments, the medical device may comprise G. The abbreviation "G" refers to polyglycolide. In some embodiments, the medical device may comprise PEG. The abbreviation "PEG" refers to poly(ethylene glycol). In some embodiments, the medical device may comprise PLGA. The abbreviation "PLGA" refers to poly(lactide-co-glycolide) also known as poly(lactic-co-glycolic acid), which are used interchangeably. In some embodiments, the medical device may comprise PLA. The abbreviation "PLA" refers to polylactide. In some embodiments, the medical device may comprise POE. The abbreviation "POE" refers to poly (orthoester).

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The section headings are not meant to limit the disclosure and one section heading can be combined with other section headings.

Anabolic Agent

An anabolic agent is a molecule that promotes the storage of protein and/or the growth of tissue. Anabolic agents include human growth hormone, insulin-like growth factor-1, insulin, stanozolol, nandrolone, testosterone, tibolone, fluoxymesterone, oxandrolone, anadrol, andriol, methyltestosterone, methandrostenlone, boldenone, androstenedione, dromostanolone, dihydrotestosterone, methenolone (Primobolan), norbolethone, tetrahydrogestrinone, oxymetholone, ethylestenol, trenbolone, drostanolone, mesterolone, bolandiol, calusterone, clostebol, dehydrochloromethyltestosterone, desoxymethyltestosterone, furazabol, 4-hydroxytestosterone, methandienone, methandriol, methasterone, methyl-1-testosterone, methynortestosterone, methyltestosterone, metribolone, mibolerone, norboletone, norclostebol, norethandorlone, quinbolone, 1-testosterone, tetrahydrogestrinone, or a combination thereof.

In some embodiments, the anabolic agent can be one or more selective androgen receptor modulators or SARMs. SARMs are a class of androgen receptor ligands. SARMs include ostarine (MK-2866), GTx-024, BMS-564,929, AC-262,356, JNJ-28330835, LGD-3303, S-40503, S-23, andarine, Ostarine™ (under development by GTx in Memphis, Tenn.) or ((2S)-3-(4-cyanophenoxy)-N-[4-cyano-3-(trifluoromethyl)phenyl]-2-hydroxy-2-methylpropanamide), flutamide, LGD2226, LGD1331, (both available from Ligand Pharmaceuticals (San Diego, Calif.)), bicalutamide, cyproterone acetate, hydroxyflutamide, spironolactone, 4-(trifluoromethyl)-2(1H)-pyrrolidono[3,2-g]quinolinone, 1,2-dihydropyridono[5,6-g]quinoline, piperidino[3,2-g]quinolinone, or pharmaceutically acceptable salts thereof, including hydrates, solvates, optical isomers, mixtures of the individual enantiomers or racemates thereof or combinations thereof.

When referring to anabolic agent, unless otherwise specified or apparent from context it is understood that the inventors are also referring to pharmaceutically acceptable equivalents or derivatives thereof, such as their pharmaceutically acceptable salts, esters, non-esters, prodrugs or active metabolites. Isomers of all disclosed agents are also encompassed by this disclosure.

Some examples of pharmaceutically acceptable salts include those salt-forming acids and bases that do not substantially increase the toxicity of a compound, such as, salts of alkali metals such as magnesium, potassium and ammonium, salts of mineral acids such as hydriodic, hydrochloric, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

A prodrug includes those derivatives of the anabolic steroid which undergo in vivo metabolic biotransformation, by enzymatic or nonenzymatic processes, such as hydrolysis, or when in contact with an esterase that form the active anabolic steroid or active metabolite. Typical prodrugs include ester and ether moieties. Prodrugs can be employed to improve pharmaceutical or biological properties, as for example solubility, melting point, stability, related physicochemical properties, absorption, pharmacodynamics or other delivery-related properties. An example of a prodrug of an anabolic agent includes, but is not limited to, fluoxymesterone (prodrug of methyltestosterone).

Further, when referring to anabolic agent and other active ingredients, they may not only be in the salt form, but also in the base form (e.g., free base). Pharmaceutically acceptable salts of anabolic agent include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, or the like.

When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, or the like. Fatty acid salts may also be used, eg., fatty acid salts having greater than 2 carbons, greater than 8 carbons or greater than 16 carbons, such as butyric, caprioc, caprylic, capric, lauric, mystiric, palmitic, stearic, arachidic or the like.

In some embodiments, the anabolic agent comprises an anabolic steroid. Anabolic steroids include stanozolol, nandrolone, testosterone, tibolone, fluoxymesterone, oxandrolone, anadrol, andriol, methyltestosterone, methandrostenlone, boldenone, androstenedione, dromostanolone, dihydrotestosterone, methenolone, norbolethone, tetrahydrogestrinone, oxymetholone, ethylestenol, trenbolone, drostanolone, primobolan, mesterolone, esterified forms, non-esterified forms or a combination thereof.

Esters of the anabolic steroid include cypionate, enanthate, propionate, heptylate; caproate, isocaproate, phenylpropionate, isocaproate, octydecanoate, decanoate, acetate, undecylenate, undecanoate esters or a combination thereof. Therefore, the anabolic steroid can be stanozolol, nandrolone, testosterone, tibolone, fluoxymesterone, oxandrolone, anadrol, andriol, methyltestosterone, methandrostenlone, boldenone, androstenedione, dromostanolone, dihydrotestosterone, methenolone, norbolethone, tetrahydrogestrinone, oxymetholone, ethylestenol, trenbolone, drostanolone, primobolan, mesterolone, bolandiol, calusterone, clostebol, dehydrochloromethyltestosterone, desoxymethyltestosterone, furazabol, 4-hydroxytestosterone, methandienone, methandriol, methasterone, methyl-1-testosterone, methynortestosterone, methyltestosterone, metribolone, mibolerone, norboletone, norclostebol, norethandorlone, quinbolone, 1-testosterone, tetrahydrogestrinone, or a combination thereof in a form that does not contain an ester or a form that contains one or more esters thereof including cypionate, enanthate, propionate, heptylate; caproate, isocaproate, phenylpropionate, isocaproate, octydecanoate, decanoate, acetate, undecylenate, undecanoate esters or a combination thereof.

In some embodiments, the anabolic steroid can be stanozolol, nandrolone, nandrolone decanoate, nandrolone octydecanoate, nandrolone undecanoate (dynabol), testosterone, tibolone, fluoxymesterone (prodrug of methyltestosterone), oxandrolone, anadrol, andriol, methyltestosterone, aquaviron (unesterfied testosterone), testosterone cypionate, enanthate, propionate, heptylate; caproate, phenylpropionate, isocaproate, decanoate, or acetate, sustanon (testosterone propionate, testosterone phenylpropionate, testosterone isocaproate, and testosterone decanoate), methandrostenlone (dianabol), boldenone, boldenone undeclynate (equipoise), androstenedione, dromostanolone, dihydrotestosterone, methenolone, norbolethone, tetrahydrogestrinone, oxymetholone, ethylestenol, trenbolone acetate, drostanolone propionate, primobolan, mesterolone, or a combination thereof.

In some embodiments, an implantable medical device is provided for treating an injury in a patient in need of such treatment, the implantable medical device comprising an anabolic agent, and at least one biodegradable polymer, the medical device having a surface that releases (i) about 50% to about 90% of the anabolic agent relative to a total amount of the anabolic agent loaded in the medical device over a first period of up to 24 hours and (ii) about 10% to about 50% of the anabolic agent relative to a total amount of the anabolic agent loaded in the medical device over a subsequent period of at least 2 days. The dosage of the anabolic agent can be given to promote anabolic properties of tissue growth and injury healing with lower or reduced androgenic effects (e.g., promoting masculine characteristics, voice deepening, growth of body hair, heart problems, liver disease, cancer, aggressive behavior, etc.).

The loading of the anabolic agent in the medical device (e.g., in percent by weight relative to the weight of the basic structure) can vary over a wide range, depending on the specific application, and can be determined specifically for the particular case. In some embodiments, the anabolic agent is in the medical device (e.g., drug depot) in an amount from about 0.1 wt. % to about 50 wt. %, or about 1 wt. % to about 30 wt. %, or about 2.5 wt. % to about 25 wt. %, or about 5 wt. % to about 25 wt. %, or about 10 wt. % to about 20 wt. %, or about 5 wt. % to about 15 wt. % based on the total weight of the medical device.

In some embodiment there is a higher loading of anabolic agent, e.g., at least 20 wt. %, at least 25%, at least 30 wt. %, at least 35%, at least 40 wt. %, at least 45%, at least 50 wt. %, at least 55%, at least 60 wt. %, at least 65%, at least 70 wt. %, at least 75%, at least 80 wt. %, at least 85%, or at least 90 wt. %.

In some embodiments, the dosage of anabolic agent may be from approximately 0.0005 to approximately 500 mg/day. In some embodiments, the amount of anabolic agent is between 1 mg, 2 mg, 3 mg, 4 mg, 5 mg, 6 mg, 7 mg, 8 mg, 9 mg and 10 mg/day. Additional dosages of anabolic agent include from approximately 0.0005 to approximately 50 µg/day; approximately 0.0005 to approximately 25 µg/day; approximately 0.0005 to approximately 10 µg/day; approximately 0.0005 to approximately 5 µg/day; approximately 0.0005 to approximately 1 µg/day; approximately 0.0005 to approximately 0.75 µg/day; approximately 0.0005 to approximately 0.5 µg/day; approximately 0.0005 to approximately 0.25 µg/day; approximately 0.0005 to approximately 0.1 µg/day; approximately 0.0005 to approximately 0.075 µg/day; approximately 0.0005 to approximately 0.05 µg/day; approximately 0.001 to approximately 0.025 µg/day; approximately 0.001 to approximately 0.01 µg/day; approximately 0.001 to approximately 0.0075 µg/day; approximately 0.001 to approximately 0.005 µg/day; approximately 0.001 to approximately 0.025 µg/day; and approximately 0.002 µg/day. In another embodiment, the dosage of anabolic agent is from approximately 0.001 to approximately 15 µg/day. In another embodiment, the dosage of anabolic agent is from approximately 0.001 to approximately 10 µg/day. In another embodiment, the dosage of anabolic agent is from approximately 0.001 to approximately 5 µg/day. In another embodiment, the dosage of anabolic agent is from approximately 0.001 to 2.5 µg/day. In some embodiments, the amount of anabolic agent is between 200 µg/day and 400 µg/day.

In one embodiment, the dosage of anabolic agent is about 0.5 mg/day to about 50 mg/day including 1 mg/day, 2 mg/day, 3 mg/day, 4 mg/day, 5 mg/day, 6 mg/day, 7 mg/day, 8 mg/day, 9 mg/day, 10 mg/day, 11 mg/day, 12 mg/day, 13 mg/day, 14 mg/day, 15 mg/day, 16 mg/day, 17 mg/day, 18 mg/day, 19 mg/day, 20 mg/day, 21 mg/day, 22 mg/day, 23 mg/day, 24 mg/day, 25 mg/day, 26 mg/day, 27 mg/day, 28 mg/day, 29 mg/day, 30 mg/day, 35 mg/day, 40 mg/day, or 45 mg/day.

In some embodiments, the anabolic agent comprises an anabolic steroid and can be administered at a dose of between 0.5 µg/kg/day (fluoxymesterone or stanozolol) through 0.1 to 3 mg/kg/day (tibolone or stanozolol) up to 10 mg/kg/day (testosterone) for prolonged periods (here in each case related to 1 kg bodyweight). For stanozolol, the natural serum level (plasma level) is approximately $10^{-8}$ M and the toxic dose is $10^{-4}$ M; in this case the practical dose range extends from approximately $10^{-8}$ M to approximately $10^{-5}$ M. Therefore, doses of stanozolol of lower than 50 mg/day can be used.

The average molecular weight of the polymer of the depot can be from about 1,000 to about 10,000,000; or about 1,000 to about 1,000,000; or about 5,000 to about 500,000; or about 10,000 to about 100,000 or about 125,000; or about 20,000 to 50,000 Daltons. In some embodiments, the molecular weight of the polymer of the depot is 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 125,000, 150,000, 175,000, 200,000, 225,000, 250,000, 275,000, 300,000, 325,000, 350,000, 375,000, 400,000, 425,000, 450,000, 475,000, 500,000, 525,000, 550,000, 575,000, 600,000, 625,000, 650,000, 675,000, 700,000, 725,000, 750,000, 775,000, 800,000, 825,000, 850,000, 875,000, 900,000, 925,000, 950,000, 975,000 and/or 1,000,000 Daltons. In various embodiments, the polymer of the depot or the depot has a molecular weight, as shown by the inherent viscosity (IV), from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

The particle size of the anabolic agent in the depot can be from about 1 to about 25 micrometers, or about 5 to 30 or 50 micrometers, however, in various embodiments ranges from about 1 micron to 250 microns may be used. In some embodiments, the particle size of the anabolic agent in the depot can be 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245 and/or 250 microns.

In one preferred embodiment, the anabolic agent does not contain an ester and comprises stanozolol in a polymer drug depot that releases about 0.5 mg to about 5 mg/kg per day. In some embodiments, the anabolic agent does not contain an ester and comprises stanozolol in a polymer drug depot that releases 0.5, 0.6, 0.7, 0.8, 0.9, 1, 2, 3, 4 or 5 mg/kg per day. The stanozolol is an active form of the anabolic steroid and does not need to be metabolized to its active form (e.g., therefore it does not need to have esters removed from it by esterase in the blood stream). In some embodiments, the stanozolol can be locally administered to the injury.

The anabolic agent or its pharmaceutically acceptable salt, esters and non-esters thereof may be administered with a muscle relaxant. Exemplary muscle relaxants include by way of example and not limitation, alcuronium chloride, atracurium bescylate, carbamate, carbolonium, carisoprodol, chlorphenesin, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The medical device (e.g., drug depot) may comprise other therapeutic agents in addition to the anabolic agent as well. These therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as glucocorticoids, antioxidants, such as dithiocarbamate, and other compounds, such as, for example, sulfasalazine.

Examples of therapeutic agents suitable for use also include, but are not limited to an anti-inflammatory agent, an analgesic agent, or an osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine[2-hydroxy-5-[-4-[C2-pyridinylamino]sulfonyl]azo]benzoic acid, sulindac, tepoxalin or tolmetin; as well as antioxidants, such as dithiocarbamate, steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivacaine, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

The therapeutic agent in the device may include, but is not limited to, members of the fibroblast growth factor family, including acidic and basic fibroblast growth factor (FGF-1 and FGF-2) and FGF-4, members of the platelet-derived growth factor (PDGF) family, including PDGF-AB, PDGF-BB and PDGF-AA; EGFs; the TGF-β superfamily, including TGF-β1, 2 or 3; osteoid-inducing factor (OIF); angiogenin(s); endothelins; hepatocyte growth factor or keratinocyte growth factor; members of the bone morphogenetic proteins (BMP's) BMP-1, BMP-3, BMP-2; OP-1, BMP-2A, BMP-2B, or BMP-7; HBGF-1 or HBGF-2; growth differentiation factors (GDF's); members of the hedgehog family of proteins, including indian, sonic and desert hedgehog; ADMP-1; other members of the interleukin (IL) family; or members of the colony-stimulating factor (CSF) family, including CSF-1, G-CSF, and GM-CSF, or isoforms thereof; or VEGF, NELL-1 (neural epidermal growth factor-like 1), CD-RAP (cartilage-derived retinoic acid-sensitive protein) or combinations thereof.

In some embodiments, the device comprises osteogenic proteins. Exemplary osteogenic proteins include, but are not limited to, OP-1, OP-2, OP-3, BMP-2, BMP-3, BMP-3b, BMP-4, BMP-5, BMP-6, BMP-9, BMP-10, BMP-11, BMP-12, BMP-13, BMP-14, BMP-15, GDF-1, GDF-2, GDF-3, GDF-5, GDF-6, GDF-7, GDF-8, GDF-9, GDF-10, GDF-11, GDF-12, CDMP-1, CDMP-2, CDMP-3, DPP, Vg-1, Vgr-1, 60A protein, NODAL, UNIVIN, SCREW, ADMP, NEURAL, and TGF-beta. As used herein, the terms "morphogen," "bone morphogen," "BMP," "osteogenic protein" and "osteogenic factor" embrace the class of proteins typified by human osteogenic protein 1 (hOP-1).

Exemplary growth factors include, but are not limited to, members of the transforming growth factor beta family, including bone morphogenetic protein 2 (BMP-2); bone morphogenetic protein 4 (BMP-4); and transforming growth factors beta-1, beta-2, and beta-3 (potent keratinocyte growth factors). Other useful members of the transforming growth factor beta family include BMP-3, BMP-5, BMP-6, BMP-9, DPP, Vg1, Vgr, 60A protein, GDF-1, GDF-3, GDF-5, GDF-6, GDF-7, CDMP-1, CDMP-2, CDMP-3, BMP-10, BMP-11, BMP-13, BMP-15, Univin, Nodal, Screw, ADMP, Neural, and amino acid sequence variants thereof. Other growth factors include epidermal growth factor (EGF), which induces proliferation of both mesodermal and ectodermal cells, particularly keratinocytes and fibroblasts; platelet-derived growth factor (PDGF), which exerts proliferative effects on mesenchymal cells; fibroblast growth factor (FGF), both acidic and basic; and insulin-like growth factor 1 (IGF-1) or 2 (IGF-2), which mediate the response to growth hormone, particularly in bone growth. Further growth factors include osteogenic proteins. A particularly preferred osteogenic protein is OP-1, also known as bone morphogenetic protein 7 (BMP-7). OP-1 is a member of the transforming growth factor beta gene superfamily.

The anabolic agent may also be administered with non-active ingredients and they may be in the device with the anabolic agent. These non-active ingredients may have multi-functional purposes including the carrying, stabilizing, pore forming agents, and/or plasticizers controlling the release of the therapeutic agent(s). Plasticizers include polyhydroxy compounds such as a carbohydrate, a polyhydroxy aldehyde, a polyhydroxy ketone, a glycogen, an aldose, a sugar, a mono- or polysaccharide, an oligosaccharide, a polyhydroxy carboxylic compound, polyhydroxy ester compound, a cyclodextrin, a polyethylene glycol polymer, a glycerol an alginate, a chitosan, a polypropylene glycol polymer, a polyoxyethylene-polyoxypropylene block copolymer, agar, or hyaluronic acid or polyhydroxy derivative compounds, hydroxypropyl cellulose, tween, sorbitan, sorbitan monolaurate, sorbitan monopalmitate, sorbitan monostearate, sorbitan tristearate, sorbitan monooleate, or a combination thereof.

The sustained release process for drug delivery using the medical device, for example, may be by a solution-diffusion mechanism or it may be governed by an erosion-sustained process. In some embodiments, the medical device (e.g., depot) will be a solid or semi-solid formulation containing a biocompatible material that can be biodegradable. In some embodiments, the medical device (e.g., depot) will be a liquid, suspension, and/or gel formulation containing a biocompatible material that can be biodegradable.

Exemplary excipients that may be formulated with the anabolic agent in addition to the biodegradable polymer include but are not limited to MgO (e.g., 1 wt. %), 5050 DLG 6E (Surmodics Pharmaceuticals, Birmingham, Ala.), 5050 DLG 1A (Surmodics Pharmaceuticals, Birmingham, Ala.), mPEG, TBO-Ac, mPEG, Span-65, Span-85, pluronic F127, TBO-Ac, sorbitol, cyclodextrin, maltodextrin, pluronic F68, CaCl, mannitol, trehalose, and combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.001 wt. % to about 10 wt. % of the formulation. In some embodiments, the excipients comprise from about 0.001 wt. % to about 5 wt. % of the formulation. In some embodiments, the excipients comprise from about 0.001 wt. % to about 2 wt. % of the formulation. In some embodiments, the excipients comprise 0.001, 0.005, 0.010, 0.015, 0.020, 0.025, 0.050, 0.075, 0.10, 0.25, 0.50, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 wt. % of the formulation.

In various embodiments, the non-active ingredients will be durable within the tissue site for a period of time equal to or greater than (for biodegradable components) or greater than (for non-biodegradable components) the planned period of drug delivery.

In some embodiments, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s). Non-biodegradable polymers include but are not limited to PVC and polyurethane.

In some embodiments, the drug depot may not be fully biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics, methacrylates, poly (N-isopropylacrylamide), PEO-PPO-PEO (pluronics) or combinations thereof. Typically, these types of drug depots may need to be removed after a certain amount of time.

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bioerodible, a bioabsorbable, and/or a biodegradable biopolymer that may provide immediate release, or sustained release of the anabolic agent. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) poly(lactide-co-glycolide) (PLGA), polylactide (PLA), polyglycolide (PGA), D-lactide, D,L-lactide, L-lactide, D,L-lactide-co-ϵ-caprolactone, D,L-lactide-co-glycolide-co-ϵ-caprolactone, poly(D,L-lactide-co-caprolactone), or poly(L-lactide-co-caprolactone), or copolymers thereof or combinations thereof. PEG may be used as a plasticizer for PLGA, but other polymers/excipients may be used to achieve the same effect. PEG imparts malleability to the resulting formulations. In some embodiments, these biopolymers may also be coated on the drug depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the drug from the depot. In some embodiments, the range of the coating on the drug depot ranges from about 5 microns to about 250 microns or 5 microns to about 200 microns to delay release from the drug depot. In some embodiments, the coating on the drug depot is 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245 and/or 250 microns.

In various embodiments, the drug depot comprises poly (lactide-co-glycolide) (PLGA), polylactide (PLA), polyglycolide (PGA), D-lactide, D,L-lactide, L-lactide, D,L-lactide-co-ϵ-caprolactone, D,L-lactide-co-glycolide-co-ϵ-caprolactone, poly(lactide-co-glycolide) (PLGA), polylactide (PLA), polyglycolide (PGA), D-lactide, D,L- lactide, L-lactide, D,L-lactide-co-ε-caprolactone, D,L-lactide-co-glycolide-co-ε-caprolactone, poly(D,L-lactide-co-caprolactone), or poly(L-lactide-co-caprolactone), or copolymers thereof or a combination thereof.

In some embodiments, the drug depot comprises one or more polymers (e.g., PLA, PLGA, etc.) having a molecular weight of from about 15,000 to about 150,000 Da or from about 25,000 to about 100,000 Da. In some embodiments, the one or more polymers have molecular weights of 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 105,000, 110,000, 115,000, 120,000, 125,000 130,000, 135,000, 140,000, 145,000, and/or 150,000 Da.

In some embodiments, the implantable depot compositions having a blend of polymers with different end groups are used the resulting formulation will have a lower burst index and a regulated duration of delivery. For example, one may use polymers with acid (e.g., carboxylic acid) and ester end groups (e.g., methyl or ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower initial burst and a regulated duration of delivery.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfate, sodium thiosulfate, thimerosal, methylparaben, polyvinyl alcohol and phenylethyl alcohol; solubility adjusting agents; stabilizers; and/or cohesion modifiers. If the depot is to be placed in the spinal area, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film or sheet (e.g., ribbon-like) or the like. Flexibility may be a consideration so as to facilitate placement of the drug depot. In various embodiments, the drug depot can be different sizes, for example, the drug depot may be a length of from about 0.5 mm to 5 mm, or 1.0 mm, 1.5 mm, 2.0 mm, 2.5 mm, 3.0 mm, 3.5 mm, 4.0 mm, 4.5 mm and have a diameter of from about 0.01 to about 4 mm, for example, 0.25 mm, 0.5 mm, 0.75 mm, or 1.0 mm, 1.25 mm, 1.5 mm, 1.75 mm, 2.0 mm, 2.5 mm, 3.0 mm, 3.5 mm, or 4.0 mm. In various embodiments, as the diameter decreases, the surface area that comes in contact with the bodily fluid of the depot increases and therefore release of the drug from the depot increases. In various embodiments, the drug depot may have a layer thickness of from about 0.005 to 1.0 mm, such as, for example, from 0.05 to 0.75 mm.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, bismuth, iodine, tantalum, tungsten, and/or metal beads or particles. In various embodiments, the radiographic marker could be a spherical shape or a ring around the depot.

Gel

In various embodiments, the anabolic agent is administered in a gel. The gel may have a pre-dosed viscosity in the range of about 1 to about 2000 centipoise (cps), 1 to about 200 cps, or 1 to about 100 cps. In some embodiments, the gel may have a pre-dosed viscosity of 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975 or 2000 cps. After the gel is administered to the target site, the viscosity of the gel will increase and the gel will have a modulus of elasticity (Young's modulus) in the range of about $1 \times -10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, a depot comprises an adherent gel comprising anabolic agent that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1\times-10^2$ to about $3\times10^5$ dynes/cm$^2$, or $2\times10^4$ to about $2\times10^5$ dynes/cm$^2$, or $5\times10^4$ to about $1\times10^5$ dynes/cm$^2$. The post-dosed hardening gels (after delivery) may have a rubbery consistency and have a modulus of elasticity in the range of about $1\times-10^2$ to about $2\times10^6$ dynes/cm$^2$, or $1\times10^5$ to about $7\times10^5$ dynes/cm$^2$, or $2\times10^5$ to about $5\times10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polymer comprises 20 wt. % to 90 wt. % of the formulation. In some embodiments, the polymer comprises 40 wt. % to 95 wt. % of the formulation. In some embodiments, the polymer comprises 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95 wt. % of the formulation.

In various embodiments, the molecular weight of the gel can be varied by many methods known in the art. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, incorporation of chain transfer or chain capping agents and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition that includes a low-molecular weight polymer. Polymeric gel formulations that include high molecular weight polymers, also tend to have a higher solution viscosity than a polymeric gel that includes low-molecular weight polymers. In various embodiments, the molecular weight of the polymer can be a wide range of values.

The average molecular weight of the polymer can be from about 1,000 to about 10,000,000; or about 1,000 to about 1,000,000; or about 5,000 to about 500,000; or about 10,000 to about 100,000; or about 20,000 to 50,000 g/mol. In some embodiments, the molecular weight of the polymer is 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 125,000, 150,000, 175,000, 200,000, 225,000, 250,000, 275,000, 300,000, 325,000, 350,000, 375,000, 400,000, 425,000, 450,000, 475,000, 500,000, 525,000, 550,000, 575,000, 600,000, 625,000, 650,000, 675,000, 700,000, 725,000, 750,000, 775,000, 800,000, 825,000, 850,000, 875,000, 900,000, 925,000, 950,000, 975,000 and/or 1,000,000 Daltons.

When the gel is designed to be a flowable gel, it can vary from low viscosity, similar to that of water, to high viscosity, similar to that of a paste, depending on the molecular weight and concentration of the polymer used in the gel. The viscosity of the gel can be varied such that the polymeric composition can be applied to a patient's tissues by any convenient technique, for example, by brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and may have a longer degradation time). Typically, when the polymers have similar components but different molecular weights, a gel with a high molecular weight provides a stronger matrix and the matrix takes more time to degrade. In contrast, a gel with a low molecular weight degrades more quickly and provides a softer matrix. In various embodiments, the polymer of the depot or the depot has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

In some embodiments, if the polymer materials have different chemistries (e.g., high molecular weight DLG 5050 and low molecular weight DL), the high molecular weight polymer may degrade faster than the low molecular weight polymer.

In various embodiments, the gel can have a viscosity of about 300 to about 5,000 centipoise (cp). In other embodiments, the gel can have a viscosity of from about 5 to about 300 cps, from about 10 cps to about 50 cps, or from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly (methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyetherurethane, or a combination thereof.

In various embodiments, rather than directly admixing the therapeutic agent into the gel, microspheres may be dispersed within the gel, the microspheres being loaded with anabolic agent. In one embodiment, the microspheres provide for a sustained release of the anabolic agent. In yet another embodiment, the gel, which is biodegradable, prevents the microspheres from releasing the anabolic agent; the microspheres thus do not release the anabolic agent until they have been released from the gel. For example, a gel may be deployed around a target tissue site (e.g., a nerve root). Dispersed within the gel may be a plurality of microspheres that encapsulate the desired therapeutic agent. Certain of these microspheres degrade once released from the gel, thus releasing the anabolic agent.

Microspheres, much like a fluid, may disperse relatively quickly, depending upon the surrounding tissue type, and hence disperse the anabolic agent. In some situations, this may be desirable; in others, it may be more desirable to keep the anabolic agent tightly constrained to a well-defined target site. The present invention also contemplates the use of adherent gels to so constrain dispersal of the therapeutic agent. These gels may be deployed, for example, at or near the injury, in a disc space, in a spinal canal, or in surrounding tissue.

In some embodiments, the anabolic agent can be dispersed in a gel and can be applied accurately to the injury, providing a continuous, uninterrupted covering over the injury. The entire injury is thereby subjected to the improved healing environment created by the gel, and the injury can heal evenly and consistently throughout. Gels can be made to stay where applied, providing prolonged control of the healing environment.

In some embodiments, when the injury-treating gel is used, an injury to be treated is cleaned before application of the present injury-treating gel. The gel can be applied directly to the injury site, in a quantity sufficient to form a continuous covering over the injury. The thickness of the layer of injury-treating gel can be from about one-eighth to about one-quarter inch thick. The covering should be changed as necessary to maintain a continuous, moist covering over the injury. External bandaging also can be used to cover the layer of injury-treating gel.

In some embodiments, the anabolic agent is in a topical formulation that can be applied to the injury (e.g., skin injury). In some embodiments, the topical formulations can take the form of an ointment, cream, lotion, paste, gel, spray, aerosol, solution, suspension or oil containing the anabolic agent. The anabolic agent can be loaded in the topical formulation in an amount of from about 1 wt % to about 25 wt %, or about 5 wt. % to about 10 wt. %. In some embodiments, the amount can be from about 10 wt. % to about 20 wt. %. In some embodiment there is a higher loading of anabolic agent, e.g., at least 20 wt. %, at least 30 wt. %, at least 40 wt. %, at least 50 wt. %, at least 60 wt. %, at least 70 wt. %, at least 80 wt. %, or at least 90 wt. %. In some embodiments, the anabolic agent can be loaded in the topical formulation in an amount of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 wt. %.

Carriers which may be used with the anabolic agent include Vaseline, lanolin, polyethylene glycols, alcohols, transdermal enhancers, or combinations of two or more thereof. Compositions suitable for transdermal administration may be presented as discrete patches adapted to remain in intimate contact with the epidermis of the recipient for a prolonged period of time. Compositions suitable for transdermal administration may also be delivered by iontophoresis. See, for example, Pharmaceutical Research 3:318 (1986), and typically take the form of an optionally buffered aqueous solution of the active compound.

In some embodiments, topical formulations comprise the active compound dissolved or suspended in one or more media such as mineral oil, petroleum, polyhydroxy alcohols or other bases used for topical pharmaceutical formulations. Topical formulations may be in the form of solid or liquid preparations, for spreading on a subject's skin. The topical formulation may contain other ingredient(s) including diluents, buffers, flavoring, coloring and aromatizing agents, binders, disintegrants, surface active agents, thickeners, lubricants, emulsifiers, surfactants, emollients, preservatives (including anti-oxidants), or the like.

Drug Delivery

It will be appreciated by those with skill in the art that the medical device (e.g., drug depot) can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflammed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655 (mm) The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

In various embodiments, a kit is provided that may include additional parts along with the drug depot and/or medical device combined together to be used to implant the drug depot. The kit may include the drug depot device in a first compartment. The second compartment may include a canister holding the drug depot and any other instruments needed for the localized drug delivery. A third compartment may include gloves, drapes, injury dressings and other procedural supplies for maintaining sterility of the implanting process, as well as an instruction booklet. A fourth compartment may include additional cannulas and/or needles. A fifth compartment may include an agent for radiographic imaging or one or more bolus doses of the steroid. Each tool may be separately packaged in a plastic pouch that is radiation sterilized. A cover of the kit may include illustrations of the implanting procedure and a clear plastic cover may be placed over the compartments to maintain sterility.

In various embodiments, a method for delivering a therapeutic agent into a site of a patient is provided, the method comprising inserting a cannula at or near a target tissue site and implanting the drug depot at the target site beneath the skin of the patient and brushing, dripping, injecting, or painting the gel in the target site to hold or have the drug depot adhere to the target site. In this way unwanted migration of the drug depot away from the target site is reduced or eliminated.

In various embodiments, to administer the gel having the drug depot dispersed therein to the desired site, first the cannula or needle can be inserted through the skin and soft tissue down to the target tissue site and the gel administered at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required, a subsequent layer or layers of gel can be applied on the drug depot to surround the depot and further hold it in place.

Alternatively, the drug depot may be implanted first and then the gel placed around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

In some embodiments, an implantable drug depot is provided for treating an injury in a patient in need of such treatment, the implantable drug depot comprising an anabolic agent, and at least one biodegradable polymer, the implantable drug depot having a surface that releases (i) about 30% to about 50% of the anabolic agent relative to a total amount of the anabolic agent loaded in the drug depot over a first period of up to 12 hours and (ii) about 50% to about 70% of the anabolic agent relative to a total amount of the anabolic agent loaded in the drug depot over a subsequent period of at least 2 days.

Injectable Anabolic Agent Formulation

The anabolic agent formulation may be designed to provide immediate release and/or sustained release of the anabolic agent at or near or in the injury and, in some embodiments, the anabolic agent may be injected. For example, the anabolic agent formulation may be a liquid injection formulation (e.g., stanozolol aqueous injection).

The anabolic agent can be formulated as suspensions or solutions in an aqueous carrier, suspensions or solutions in an oily or alcoholic carrier, in glycosaminoglycans, especially hyaluronic acid (sodium hyaluronan), or in dimethyl sulphoxide or other suitable formulation.

To aid in solubilizing the anabolic agent, the anabolic agent can be micronized to sizes of from about 1 micron to 250 microns or about 10 microns to 100 microns or about 20 microns to 100 microns or about 2 microns to 10 microns. The anabolic agent can be amorphous, or in crystallized form or a combination thereof. In some embodiments, the anabolic agent can be micronized to 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245 and/or 250 microns.

The anabolic agent can be packed in a unit dose vial for the application of a liquid formulation to an injury and can contain enough anabolic agent to be therapeutically effective for a human. In certain embodiments, the single unit dose vial or preloaded syringe of the anabolic agent is suitable for use in administering the composition to either the cerebrospinal system, or to the musculoskeletal system or to the skin or where ever an injury is present.

In some embodiments, the anabolic agent may be administered in a total volume of about 10 microliters to about 60 ml, or about 100 microliters to about 20 ml. The dose may also have a total volume of about 50 microliters or less. The dose may have a total volume of or up to about 10 microliters, 15 microliters, 20 microliters, 25 microliters, 30 microliters, 35 microliters, 40 microliters, 45 microliters, 50 microliters, 55 microliters, 60 microliters, 65 microliters, 70 microliters, 75 microliters, 80 microliters, 85 microliters, 90 microliters, 95 microliters, 100 microliters, 200 microliters, 300 microliters, 400 microliters, 500 microliters, 600 microliters, 700 microliters, 800 microliters, 900 microliters, or 1 ml or intermediate dosages. The dose may have a total volume greater than 1 ml, such as 1.1 ml, 1.2 ml, 1.3 ml, 1.4 ml, 1.5 ml, 1.6 ml, 1.7 ml, 1.8 ml, 1.9 ml, 2 ml, or more than about 2 ml, as well as intermediate dosages.

In some embodiments, the anabolic agent is administered in a single injection or, alternatively and less preferably, in multiple injections, wherein multiple unit doses may be administered to the patient at the discretion of the treating physician based on the patient's size, type of injury, medical condition, or other relevant criteria in determining the appropriate dosage.

In some embodiments, one or more injections of the anabolic agent can be made at near or in the injury to enhance injury healing. The anabolic agent may be in aqueous form or be in a polymer based depot or may be in administered by continuous infusion through a pump.

According to some embodiments, only a single dose of the anabolic agent is given. According to other embodiments, multiple doses of the anabolic agent are given. When multiple doses are given, they may for example, be given over about 1 to about 24 hours or every other day or every three days or every week or every month depending on the injury. In some embodiments, when multiple doses of the anabolic agent are given, they may be given over 1, 2, 3, 4, 5, 6, 7, 8, 9, 10, 11, 12, 13, 14, 15, 16, 17, 18, 19, 20, 21, 22, 23 or 24 hours.

In some embodiments, the anabolic formulation is free from classical preservatives and/or free of dispersion agents. In some embodiments, the anabolic agent formulation comprises, consists of or consists essentially of the active ingredient (or its pharmaceutically acceptable salt or ester thereof), water and optionally a suitable excipient.

Exemplary excipients for the anabolic agent formulation include but are not limited to methylcellulose, hydroxypropylmethylcellulose, hydroxyethylcellulose, polyvinyl alcohol, propylene glycol, and polyethylene glycol. In some embodiments, the anabolic agent formulation may for example contain a minimum excipient concentration of at least about 0.2%, or at least about 0.35%, or at least about 0.5%, wherein the percentages are measured in weight per volume. Additionally, in some embodiments, the anabolic agent formulation may contain a maximum excipient concentration of about 5%, or about 2%, or about 1% excipient, wherein these percentages are measured in weight per volume.

In some embodiments, when the active ingredient in the liquid formulation is an anabolic agent, the anabolic agent and excipient may be carried by an aqueous carrier, which may be a combination of a salt and water. Any suitable salt can be employed; however, the salt should be acceptable for pharmaceutical use in the concentration employed to treat the injury. The salt may for example be sodium chloride. The pharmaceutical composition preferably contains at least about 0.7% (w/v) sodium chloride and no more than about 1.1% (w/v) sodium chloride (e.g., about 0.8-1% (w/v)). More preferably, the pharmaceutical composition contains about 0.9% sodium chloride. Additionally, the salt concentration or excipient concentration or both are preferably adjusted, if necessary, to provide an osmolarity of from about 200 mOsm to about 400 mOsm.

In some embodiments, the active ingredient (e.g., anabolic agent, etc.) may be in powder form and can be reconstituted with one or more liquid diluents that may be aqueous. For example, an aqueous liquid diluent may be water, pharmaceutically acceptable aqueous solutions, aqueous saline solutions (NS, ½ NS, etc.), Ringer's solutions, lactated Ringer's solutions, bicarbonate solutions, or aqueous dextrose solutions, or combinations thereof. The liquid diluent may contain one or more excipients such as the antioxidant BHT (butylated hydroxytoluene).

In another embodiment, the liquid diluent is non-aqueous and comprises one or more surfactants, e.g., non-ionic surfactants. In general, the weight to weight ratio (w/w)

between the active ingredient or a salt thereof and the non-ionic surfactant(s) may be from about 1:10,000 to about 1:1. Useful non-ionic surfactants can include a polyethoxylated castor oil, a polysorbate, a sorbitan ester, a polyoxyethylene fatty acid ester, a polyoxyethylene fatty acid ether, a polyoxyethylene alkyl ether, or an ethoxylated fatty acid.

In other embodiments, a liquid diluent may be a combination of aqueous diluents and non-aqueous diluents. For example, a non-aqueous liquid diluent comprising one or more non-ionic surfactants may further include an aqueous diluent, such as water, pharmaceutically acceptable aqueous solutions, aqueous saline solutions, Ringer's solutions, lactated Ringer's solutions, bicarbonate solutions, aqueous dextrose solutions, or combinations thereof. In a specific embodiment, the volume to volume ratio (v/v) of non-ionic surfactant to aqueous diluent may be from about 100:1 to about 1:20,000.

When the liquid formulation comprises both the anabolic agent and another agent such as an anti-inflammatory agent, they can be mixed in it, all or a fraction of each of the above-described formulation may be combined in the same syringe or co-administered through different syringes.

The anabolic agent formulation of the present application may be used as medicaments in the form of pharmaceutical preparations. The preparations may be formed in an administration with a suitable pharmaceutical carrier that may be solid or liquid and organic or inorganic, and placed in the appropriate form for parenteral or other administration as desired. Carriers for the active pharmaceutical ingredient include but are not limited to water, saline solution, gelatin, lactose, starches, stearic acid, magnesium stearate, sicaryl alcohol, talc, vegetable oils, benzyl alcohols, gums, waxes, propylene glycol, polyalkylene glycols or other carriers for medicaments.

Parenteral administration may additionally include, for example, an infusion pump that administers a pharmaceutical composition (e.g., anabolic agent) through a catheter at or near the injury or an implantable mini-pump that can be inserted at or near the injury, an implantable controlled release device or sustained release delivery system that can release a certain amount of the anabolic agent per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas that provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, continually, at specific times, or at set intervals between deliveries.

In some embodiments, the anabolic agent is encapsulated in a plurality of depots comprising microparticles, microspheres, microcapsules, and/or microfibers.

In some embodiments there is a method for making an implantable drug depot. The method may comprise combining a biocompatible polymer and a therapeutically effective amount of anabolic agent or a pharmaceutically acceptable salt thereof and forming the implantable drug depot from the combination.

In some embodiments, the anabolic agent is suitable for parenteral administration. The term "parenteral" as used herein refers to modes of administration that bypass the gastrointestinal tract, and include for example, intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof. In some embodiments, the injection is intrathecal, which refers to an injection into the spinal canal (intrathecal space surrounding the spinal cord). An injection may also be into a muscle or other tissue.

Method of Making

In various embodiments, the drug depot comprising the anabolic agent can be made by combining a biocompatible polymer and a therapeutically effective amount of anabolic agent or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: an anabolic agent and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: anabolic agent, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, anabolic agent may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the anabolic agent containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., anabolic agent), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of anabolic agent because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet) is cooled. Examples of cooling processes include air cooling and/or immersion in a cooling bath. In some embodiments, a water bath is used to cool the extruded depot. However, where a water-soluble therapeutic agent such as anabolic agent are used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired. Otherwise, the water or moisture exposure will allow the drug to crystallize on the depot and there will be an initial burst effect In various embodiments, the drug depot can be prepared by mixing or spraying the drug with the polymer and then molding the depot to the desired shape. In various embodiments, anabolic agent is used and mixed or sprayed with the PLGA or PEG550 polymer, and the resulting depot may be formed by extrusion and dried.

In various embodiments, there is a pharmaceutical formulation comprising: anabolic agent, wherein the anabolic agent comprises from about 0.1 wt. % to about 60 wt. % of the formulation/drug depot, and at least one biodegradable polymer. In some embodiments, the anabolic agent comprises from about 5 wt. % to about 60 wt. % of the formulation/drug depot. In some embodiments, the anabolic agent comprises from about 3 wt. % to about 20 wt. % or 30 wt. %, about 3 wt. % to about 18 wt. %, about 5 wt. % to about 15 wt. % or about 7.5 wt. % to about 12.5 wt. % of the formulation. In some embodiments, the anabolic agent comprises 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 wt. % of the formulation/drug depot. By way of example, when using a 5%-15% anabolic agent composition, the mole ratio of anabolic agent to polymer would be from approximately 16-53 when using an approximately 80 lcDalton polymer that has a 267 grams/mole ratio. By way of another example, when using a 5%-15% anabolic agent base in the composition, the mole ratio of anabolic agent base to polymer would be from approximately 18-61 with a mole mass of 230 g/mol. In some embodiments, the weight ratio will be in the range of 10-50% assuming a target dose anabolic dose of ~1 mg/d for 14 days.

In some embodiments, the drug depot comprises at least one biodegradable material in a wt % of about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot and the remainder is active and/or inactive pharmaceutical ingredients.

In some embodiments, the at least one biodegradable polymer comprises poly(lactic-co-glycolide) (PLGA) or poly(orthoester) (POE) or a combination thereof. The poly(lactic-co-glycolide) may comprise a mixture of polyglycolide (PGA) and polylactide and in some embodiments, in the mixture, there is more polylactide than polyglycolide. In various embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In some embodiments, the at least one biodegradable polymer comprises poly(D,L-lactide-co-caprolactone), or poly(L-lactide-co-caprolactone) or copolymers thereof or a combination thereof. The molar ratio of D,L-lactide or L-lactide to caprolactone in the poly(D,L-lactide-co-caprolactone), or poly(L-lactide-co-caprolactone) is 95% D,L-lactide or L-lactide and 5% caprolactone; 90% D,L-lactide or L-lactide and 10% caprolactone; 85% D,L-lactide or L-lactide and 15% caprolactone; 80% D,L-lactide or L-lactide and 20% caprolactone; 75% D,L-lactide or L-lactide and 25% caprolactone; 70% D,L-lactide or L-lactide and 30% caprolactone; 65% D,L-lactide or L-lactide and 35% caprolactone; 60% D,L-lactide or L-lactide and 40% caprolactone; 55% D,L-lactide or L-lactide and 45% caprolactone; 50% D,L-lactide or L-lactide and 50% caprolactone; 45% D,L-lactide or L-lactide and 55% caprolactone; 40% D,L-lactide or L-lactide and 60% caprolactone; 35% D,L-lactide or L-lactide and 65% caprolactone; 30% D,L-lactide or L-lactide and 70% caprolactone; 25% D,L-lactide or L-lactide and 75% caprolactone; 20% D,L-lactide or L-lactide and 80% caprolactone; 15% D,L-lactide or L-lactide and 85% caprolactone; 10% D,L-lactide or L-lactide and 90% caprolactone; or 5% D,L-lactide or L-lactide and 95% caprolactone or copolymers thereof or combinations thereof. In various embodiments, the medical device comprises polymers and copolymers containing various molar ratios of PEG, lactide, glycolide and/or caprolactone.

In various embodiments, the drug particle size (e.g., anabolic agent) is from about 1 to about 25 micrometers, or about 5 to 50 micrometers, however, in various embodiments ranges from about 1 micron to 250 microns may be used.

In some embodiments, at least 75% of the particles have a size from about 10 micrometer to about 200 micrometers. In some embodiments, at least 85% of the particles have a size from about 10 micrometer to about 200 micrometers. In some embodiments, at least 95% of the particles have a size from about 10 micrometer to about 200 micrometers. In some embodiments, all of the particles have a size from about 10 micrometer to about 200 micrometers.

In some embodiments, at least 75% of the particles have a size from about 20 micrometer to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles have a size from about 20 micrometer to about 180 micrometers.

In some embodiments, the biodegradable polymer comprises at least 40 wt. %, at least 45 wt. %, at least 50 wt. %, at least 55 wt. %, at least 60 wt. %, at least 70 wt. %, at least 80 wt. %, at least 85 wt. %, at least 90 wt. %, at least 95 wt. % or at least 97 wt. % of the formulation. In some embodiments, the at least one biodegradable polymer and the anabolic agent are the only components of the pharmaceutical formulation.

In some embodiments, there is a pharmaceutical formulation comprising: an anabolic agent, wherein the anabolic agent is in non-esterified form (does not contain any ester), and comprises from about 0.1 wt. % to about 60 wt. % of the formulation, and at least one biodegradable polymer, wherein the at least one biodegradable polymer comprises poly(lactide-co-glycolide) (or poly(lactic-co-glycolic acid)) or poly(orthoester) or a combination thereof, and said at least one biodegradable polymer comprises at least 40 wt. % of said formulation.

In some embodiments, there is a pharmaceutical formulation comprising an anabolic agent, wherein the anabolic agent is stanozolol and comprises from about 5 wt. % to about 60 wt. % of the formulation and a polymer comprises at least 40% of the formulation. In some embodiments, the polymer in this formulation is polyorthoester.

In some embodiments, the formulation comprises a drug depot that comprises a biodegradable polyorthoester. The mechanism of the degradation process of the polyorthoester can be hydrolytical or enzymatical in nature, or both. In various embodiments, the degradation can occur either at the surface of the drug depot (heterogeneous or surface erosion) or uniformly throughout the drug delivery system depot (homogeneous or bulk erosion). Polyorthoester can be obtained from A.P. Pharma, Inc. (Redwood City, Calif.) or through the reaction of a bis(ketene acetal) such as 3,9-diethylidene-2,4,8,10-tetraoxospiro[5,5]undecane (DETOSU) with suitable combinations of diol(s) and/or polyol(s) such as 1,4-trans-cyclohexanedimethanol and 1,6-hexanediol or by any other chemical reaction that produces a polymer comprising orthoester moieties.

In some embodiments, there is a method for treating an injury in a patient in need of such treatment, the method comprising administering an anabolic agent locally at or near or in the injury, the anabolic agent being administered by a topical formulation, an infusion pump or local injection every day, every other day, every three days, every seven days, or every month by one dose, continuously or intermittent doses so as to enhance healing of the injury. In some embodiments, the topical formulation is a gel and the anabolic agent is administered daily over a period of about 1 to 30 days. In some embodiments, the anabolic agent is administered daily over a period of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days.

In some embodiments, a topical formulation, an infusion pump or local injection is delivered at or near or in the injury and it can be used alone or with dressings such as bandages, gauze, fabrics, meshes, sutures, catheters, sealants, ointments, creams, gels, adhesives, irrigations, hydrating agents, or the like. However, the anabolic agent can be injected, or applied at or near or in the injury to allow the injury to heal faster by days or even weeks faster. In some embodiments, the treatment can enhance or improve injury healing by 10%, 15%, 20%, 25%, 30%, 35%, 40%, 45%, 50%, 55%, 60%, 65%, 70%, 75%, 80%, 85%, 90%, 95%, or higher.

Injury treatment formulations should be sterile, to prevent contamination and infection of the injury. Known sterilizing techniques include heating, filtration and gamma irradiation. In some embodiments, the anabolic agent formulation does not contain any preservatives. In some embodiments, the anabolic agent does contain preservatives.

In some embodiments, the medical device has an anabolic agent loading of from about 1 wt % to about 25 wt %, or about 5 wt. % to about 10 wt. %. In some embodiments, the loading is from about 10 wt. % to about 20 wt. %. In some embodiments, the medical device is loaded with between about 5 wt % to about 60 wt % of the anabolic agent based on the total weight of the medical device. In some embodiments, the medical device is loaded with between about 10 wt % to about 60 wt % of the anabolic agent based on the total weight of the medical device. In some embodiments, the medical device is loaded with between about 10 wt % to about 30 wt % of the anabolic agent based on the total weight of the medical device.

In some embodiment there is a higher loading of anabolic agent, e.g., at least 20 wt. %, at least 30 wt. %, at least 40 wt. %, at least 50 wt. %, at least 60 wt. %, at least 70 wt. %, at least 80 wt. %, or at least 90 wt. %.

A strategy of triangulation may be effective when administering these pharmaceutical formulations. Thus, a plurality (at least two, at least three, at least four, at least five, at least six, at least seven, etc.) drug depots comprising the pharmaceutical formulations may be placed around the target tissue site (e.g., injury site) such that the target tissue site falls within a region that is either between the formulations when there are two, or within an area whose perimeter is defined by a set of plurality of formulations.

In some embodiments, the formulations are slightly rigid with varying length, widths, diameters, etc. For example, certain formulations may have a diameter of 0.50 mm and a length of 4 mm. It should be noted that particle size may be altered by techniques such as mort and pestle, jet-drying, jet milling, Fitz milling, or cryogrinding.

In some embodiments, anabolic agent is released daily for a period of at least three days. In some embodiments, this release rate continues for, at least seven to twenty-one days or at least one to 5 days. In some embodiments, the anabolic agent is implanted at multiple sites that triangulate the target site (e.g., injury). In some embodiments, the therapeutically effective dosage amount (e.g., anabolic agent dose) is released from the drug depot for a period of at least three days to twenty-one days. In some embodiments, the anabolic agent is a non-esterified anabolic steroid and the anabolic agent is released over a period of 1 to 5 days.

In some embodiments the anabolic agent in the depot is designed for a bolus dose or burst dose within 1, 2, or 3 days after implantation to provide an immediate release of the anabolic agent for treatment of the injury.

In some embodiments, the anabolic agent depot is administered parenterally, e.g., by injection. In some embodiments, the injection is intrathecal, which refers to an injection into the spinal canal (intrathecal space surrounding the spinal cord). An injection may also be into a muscle or other tissue. In other embodiments, the anabolic agent depot is administered by placement into an open patient cavity during surgery.

In some embodiments, the drug depot (i) comprises one or more immediate release layer(s) that is capable of releasing about 5% to about 20% of the anabolic agent or pharmaceutically acceptable salts thereof relative to a total amount of the anabolic agent or pharmaceutically acceptable salt thereof loaded in the drug depot over a first period of up to 48 hours and (ii) one or more sustain release layer(s) that is capable of releasing about 21% to about 99% of the anabolic agent or pharmaceutically acceptable salt thereof relative to a total amount of the anabolic agent or pharmaceutically acceptable salt thereof loaded in the drug depot over a subsequent period of up to 3 days to 21 days.

In some embodiments, there is a drug depot comprising anabolic agent and a polymer, wherein the polymer is one more of various embodiments, the drug depot comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone or a combination thereof.

Having now generally described the invention, the same may be more readily understood through the following reference to the following examples, which are provided by way of illustration and are not intended to limit the present invention unless specified.

EXAMPLES

In a recent proof-of-concept study, male hairless guinea pigs (n=30) receive bilateral incisions as previously described by Storch, Perry, Davidson, and Ward (Surg Infect (Larchmt) 2002; 3 Suppl 1:S89-98) This reference is herein incorporated by reference. Two linear full-thickness incisions exactly 2 cm long and separated by approximately 3 cm were made on the left and right dorsolateral regions of all animals. Incisions extend through the dermis and subcutaneous tissue and panniculus carnosus muscle. After the injuries were created, 200 μL of a 10 mg/mL aqueous suspension (1 mg of drug, ~2.7 mg/kg) of generic stanozolol was applied directly into the injury bed in the right flank but not left flank of n=16 animals. The injury bed on the left side of these animals received 200 μL of saline vehicle control. In the remaining fourteen animals, incisions were not treated (nothing applied control). Only the incision in the right flank was assessed for injury strength in the nothing applied control animals. All injuries were then closed with interrupted nylon sutures. On days 2, 4, and 6 (in remaining animals), animals in the stanozolol group received 100 μL (0.5 mg, ~1.4 mg/kg) of the same stanozolol suspension in the right injury and 100 μL of saline in the left injury, carefully injected with an insulin syringe introduced lateral to the injury and directed towards the injury bed. For each time point (days 5 and 7), injury strength was tested in 7 nothing applied control guinea pigs and 8 stanozolol guinea pigs after carefully removing dressing and sutures. Injury strength was measured by applying a vacuum to the injury and recording the pressure at which the injury fails. Biomechanical testing was performed under anesthesia using the BRC-2000™ (SRI Technologies, Nashville). A disposable acrylic test ring was placed around the injury and secured to the skin using acrylate glue. The BTC-2000™ test chamber (2.5 cm ID) was mated to the test ring. An escalating negative pressure was applied to the injury at a rate of 10 mm Hg/second, producing a multi-axial stress on the injury. Displacement of injury margins was captured by a target laser. The time-synchronized data was displayed graphically and analyzed by the BTC-2000™ in real-time. On both test days, stanozolol treated injuries were significantly stronger as compared to nothing applied control injuries. Injury strength is considered in index of injury healing. No effect was observed on contralateral injuries in stanozolol treated animals. The results are shown graphically in FIG. 1. Briefly, FIG. 1 is a bar graph illustration of accelerated surgical injury healing demonstrated in animals that received a locally injected anabolic agent (stanozolol) at a bolus dose of 1 mg initially, then 0.5 mg on days 2, 4, and 6. The surgical injuries were tested on days 5 and seven. The surgical injuries that received locally delivered stanozolol had the highest injury strength when exposed to pressure when compared to injuries with the control or placebo administered to them.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable medical device for treating an injury in a patient in need of such treatment, the implantable medical device comprising an anabolic agent comprising stanozolol, the stanozolol having a particle size of from about 5 microns to about 50 microns, and at least one biodegradable polymer, and an excipient comprising MgO, TBO—Ac (tributyl-ortho-acetylcitrate), Span-65 (sorbitan tristearate), Span-85 (sorbitan trioleate), cyclodextrin, maltodextrin, CaCl, mannitol, trehalose, or a combination thereof, the medical device having a surface that releases (i) about 50% to about 90% of the anabolic agent relative to a total amount of the anabolic agent loaded in the medical device over a first period of up to 24 hours and (ii) about 10% to about 50% of the anabolic agent relative to a total amount of the anabolic agent loaded in the medical device over a subsequent period of at least 2 days in an amount of about 0.0005 to about 50 μg.

2. An implantable medical device according to claim 1, wherein the injury comprises a traumatic soft tissue injury, surgical injuries, burn, traumatic brain injuries, musculotendinous injuries, musculoskeletal conditions, bone injury or a combination thereof and the medical device is a drug depot that is implanted at or near the injury.

3. An implantable medical device according to claim 1, wherein the anabolic agent is a non-esterified anabolic steroid and the anabolic agent is released over a period of 1 to 5 days.

4. An implantable medical device according to claim 1, wherein the anabolic agent comprises at least one of stanozolol, nandrolone, nandrolone decanoate, nandrolone octydecanoate, testosterone, tibolone, fluoxymesterone, or a combination thereof.

5. An implantable medical device according to claim 1, wherein the stanozolol is in an aqueous carrier.

6. An implantable medical device according to claim 1, wherein the anabolic agent comprises androgen receptor modulators comprising ostarine (MK-2866), GTx-024, BMS-564,929, AC-262,356, JNJ-28330835, LGD-3303, S-40503, S-23, ((2S)-3-(4-cyanophenoxy)-N-[4-cyano-3-(trifluoromethyl)phenyl]-2-hydroxy-2-methylpropanamide), flutamide, bicalutamide, cyproterone acetate, hydroxyflutamide, spironolactone, 4-(trifluoromethyl)-2 (1H)-pyrrolidone[3,2-g]quinolinone, 1,2-dihydropyridono [5,6-g]quinoline, piperidino[3,2-g]quinolinone, pharmaceutically acceptable salts, or a combination thereof.

7. An implantable medical device according to claim 1, wherein the at least one biodegradable polymer comprises at least 40 wt. % to about 95 wt. % of the medical device.

8. An implantable medical device according to claim 1, wherein the at least one biodegradable polymer comprises one or more of poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, poly(D,L-lactide-co-caprolactone), or poly(L-lactide-co-caprolactone), or copolymers thereof or a combination thereof.

* * * * *